United States Patent [19]

Inoue et al.

[11] 4,207,256

[45] Jun. 10, 1980

[54] TREATMENT OF WATER VAPOR GENERATED IN CONCENTRATING AN AQUEOUS UREA SOLUTION

[75] Inventors: Shigeru Inoue, Kanagawa; Tadao Shirasu, Chiba; Hisashi Miyagawa, Takaishi, all of Japan

[73] Assignee: Mitsui Toatsu Chemicals Inc., Tokyo, Japan

[21] Appl. No.: 651,569

[22] Filed: Jan. 22, 1976

[30] Foreign Application Priority Data

May 6, 1975 [JP] Japan .................................. 50-53141

[51] Int. Cl.$^2$ .......................................... C07C 126/02
[52] U.S. Cl. ................................................ 260/555 A
[58] Field of Search ..................................... 260/555 A

[56] References Cited

U.S. PATENT DOCUMENTS

| | | | |
|---|---|---|---|
| 3,090,811 | 6/1963 | Otsuka et al. | 260/555 A |
| 3,146,263 | 8/1964 | Otsuka | 260/555 A |
| 3,232,983 | 1/1966 | Flinn | 260/555 A |
| 3,527,799 | 9/1970 | Mavrovic | 260/555 A |
| 3,636,106 | 1/1972 | Villiers-Fisher et al. | 260/555 A |
| 3,668,250 | 6/1972 | Karafian | 260/555 A |
| 3,711,544 | 1/1973 | Summerville | 260/555 A |
| 3,824,283 | 7/1974 | Harada et al. | 260/555 A |
| 3,922,222 | 11/1975 | Van Moorsel | 260/555 A |
| 3,932,504 | 1/1976 | Chew et al. | 260/555 A |
| 3,944,605 | 3/1976 | Inoue et al. | 260/555 A |

Primary Examiner—Delbert E. Gantz
Assistant Examiner—Thomas W. Roy

[57] ABSTRACT

A process for treating water vapor generated in concentrating an aqueous urea solution wherein a urea synthesis effluent containing urea, unreacted ammonium carbamate and water from a urea synthesis zone is subjected to a plurality of decomposition stages, the pressures of which stages are stepwise reduced to decompose and separate substantially all of the unreacted ammonium carbamate from the aqueous urea solution. The aqueous urea solution which still contains small amounts of ammonia and carbon dioxide is concentrated to obtain crystalline urea or molten urea substantially free of water. The water vapor generated in concentrating said aqueous urea solution which contains small amounts of ammonia and carbon dioxide is cooled for condensation thereby forming a dilute aqueous ammonium carbamate solution which is subjected to rectification under a gauge pressure below 25 kg/cm$^2$ to distil off a gaseous mixture of water vapor, ammonia and carbon dioxide, introducing the gaseous mixture into the unreacted ammonium carbamate decomposition stage using rectification under substantially the same pressure as the pressure of the rectification for the dilute aqueous ammonium carbamate solution to remove the water vapor from the gaseous mixture, and recovering the resultant ammonia and carbon dioxide together with a gaseous mixture of ammonia and carbon dioxide which is generated in the unreacted ammonium carbamate decomposition stage.

9 Claims, 1 Drawing Figure

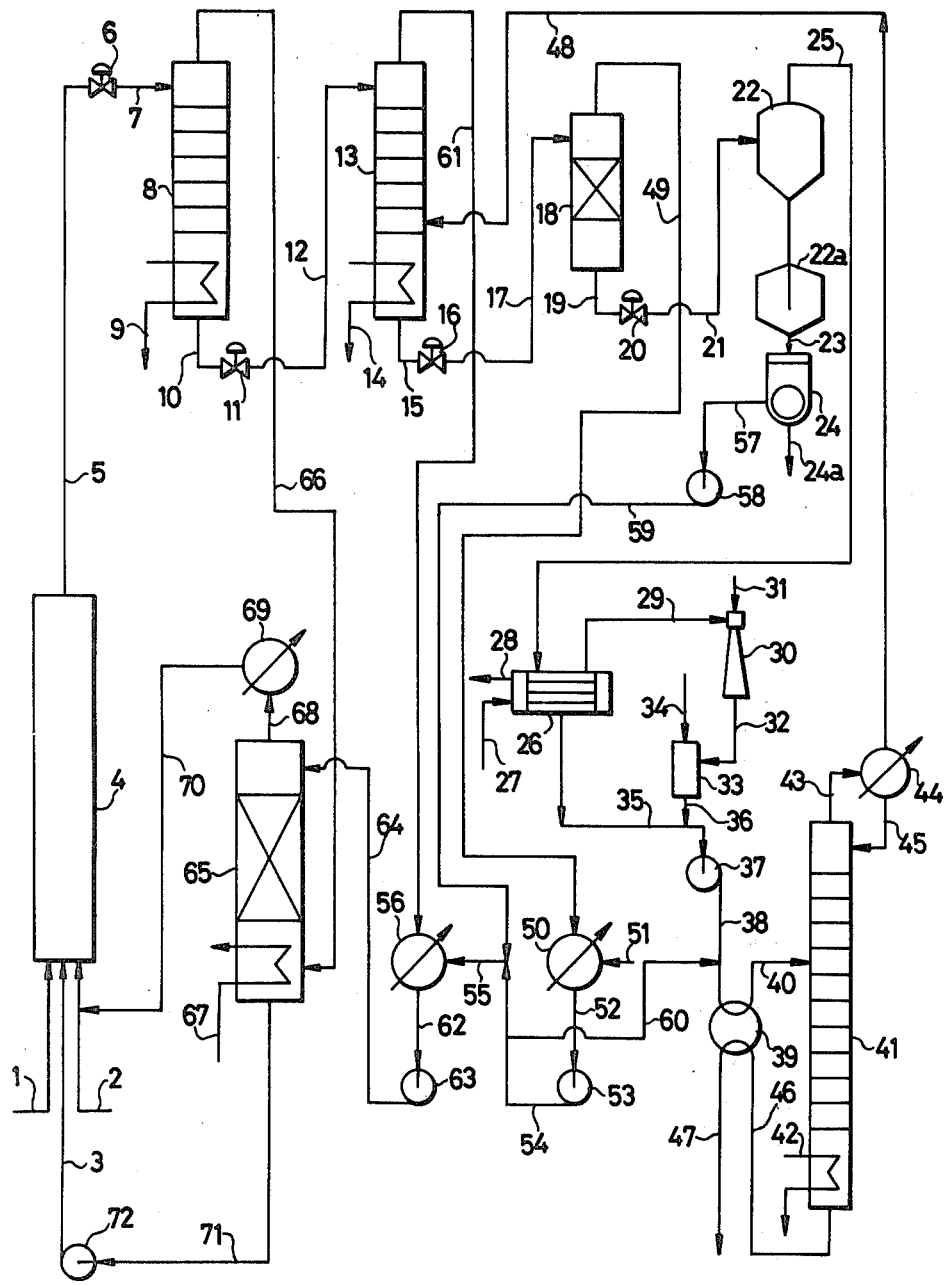

TREATMENT OF WATER VAPOR GENERATED IN CONCENTRATING AN AQUEOUS UREA SOLUTION

BACKGROUND OF THE INVENTION

1. Field of the Invention

This invention relates to a process for treating water vapor which is generated while concentrating an aqueous urea solution containing small amounts of ammonia and carbon dioxide and, more particularly, it relates to a process for recovering ammonia and carbon dioxide from water vapor which is generated while concentrating an aqueous urea solution containing small amounts of said ammonia and carbon dioxide.

2. Description of the Prior Art

The production of crystal urea or molten urea from carbon dioxide and ammonia is carried out by a process which comprises reacting carbon dioxide and ammonia under urea-forming temperatures and pressures, passing the resultant urea synthesis effluent containing urea, unreacted ammonium carbamate and water through a plurality of stages for decomposing the unreacted ammonium carbamate (such as two stages composed of one high pressure stage and one low pressure stage; three stages composed of two high pressure and one low pressure stages, or stripping by carbon dioxide or ammonia under a pressure substantially equal to a urea synthesis pressure and subsequent high and/or low pressure decomposition stage; it being general to provide a flash separation stage under an almost normal pressure or a vacuum subsequent to a low pressure decomposition stage) wherein pressure is reduced by steps in order to separate the unreacted ammonium carbamate from the reaction mixture by decomposition, and subjecting the resultant aqueous urea solution containing small amounts of ammonia and carbon dioxide to concentration under normal pressure or vacuum to separate urea as crystals, or alternatively, concentrating the urea aqueous solution containing small amounts of ammonia and carbon dioxide into substantially water-free molten urea without yielding crystal urea.

In this process, water vapor generated from a concentrator generally contains small amounts of aqueous urea solution mist, ammonia and carbon dioxide, so that discharge of the water vapor by condensing the vapor into water results not only in water pollution, but also in loss of urea and ammonia. Accordingly, it is common practice to condense the water vapor by indirectly cooling into a dilute aqueous solution of urea, ammonia and carbon dioxide, and to subject the dilute aqueous solution to rectification for separation of a gaseous mixture of ammonia, carbon dioxide and water vapor from the solution, the gaseous mixture being recovered by absorption together with an off-gas from the low pressure decomposition stage of unreacted ammonium carbamate. However, the water vapor in the gaseous mixture is large in amount, so that the absorbate obtained by the absorption of the gaseous mixture disadvantageously tends to be diluted to excess. Further, additional cooling water will be inconveniently required for removal of heat of condensation of the water vapor.

The following two processes are considered to be available for the recovery of ammonia and carbon dioxide from the water vapor discharged from the step of concentration of the aqueous urea solution for reuse in urea synthesis. The first process includes condensing the water vapor to form a dilute aqueous ammonium carbamate solution and subjecting the aqueous solution to decomposition together with urea synthesis effluent containing unreacted ammonium carbamate under high or low pressure to decompose the ammonium carbamate contained in the dilute aqueous ammonium carbamate solution as well as unreacted ammonium carbamate.

In this process, however, all of the water vapor from the concentration step of the aqueous urea solution is fed to the decomposition step and the water vapor from the concentration step gradually increases in amount, the aqeous urea solution being finally excessively diluted. In order to avoid the excessive dilution, it is required either to discard part of the water vapor from the system or to provide an additional system for recovering ammonia and carbon dioxide from the water vapor.

In the second process, the water vapor fed from the concentration step is compressed and subjected to low pressure decomposition for condensation of most of the water vapor and for collection of ammonia and carbon dioxide involved as well as ammonia and carbon dioxide which are formed in decomposition of unreacted ammonium carbamate. However, this process has the same disadvantage as the first process. Moreover, ammonia and carbon dioxide are also unavoidably condensed together with part of water vapor in compressing the gaseous mixture. Accordingly, it is necessary to prevent ammonia and carbon dioxide from being condensed, requiring a complicated apparatus.

It is therefore an object of the present invention to provide an improved process for the recovery of ammonia and carbon dioxide from water vapor generated in concentrating an aqueous urea solution.

SUMMARY OF THE INVENTION

It has been found that the above object can be attained by an improvement in the process for treating water vapor generated in concentrating an aqueous urea solution wherein a urea synthesis effluent containing urea, unreacted ammonium carbamate and water from a urea synthesis zone is subjected to a plurality of unreacted ammonium carbamate decomposition stages, the pressures of which are stepwise reduced to decompose and separate substantially all of the unreacted ammonium carbamate from the aqueous urea solution, and the aqueous urea solution which still contains small amounts of ammonia and carbon dioxide is concentrated to obtain crystal urea or molten urea substantially free of water. The improvement comprises cooling for condensation, water vapor which is generated in concentrating the aqueous urea solution and which contains small amounts of ammonia and carbon dioxide thereby forming a dilute aqueous ammonium carbamate solution, subjecting the dilute aqueous ammonium carbamate solution to rectification under a gauge pressure below 25 $kg/cm^2$ to distill off a gaseous mixture of water vapor, ammonia and carbon dioxide, introducing the gaseous mixture into the unreacted ammonium carbamate decomposition stage using a rectification under substantially the same pressure as the pressure of the rectification for the dilute aqueous ammonium carbamate solution to remove the water vapor from the gaseous mixture, and recovering the resultant ammonia and carbon dioxide together with a gaseous mixture of ammonia and carbon dioxide which is generated in the unreacted ammonium carbamate decomposition stage.

The process of the invention is applicable not only to a urea synthesis with solution recycle, but also to a urea synthesis with a hot gas recycle described in the U.S. Pat. No. 3,200,148, a urea synthesis with an ammonium carbamate slurry recycle, or a once-through type urea synthesis. In other words, the process of the invention can be applied to any urea synthesis process provided that the process include a rectification step at a gauge pressure below 25 kg/cm$^2$ in which unreacted ammonium carbamate contained in the urea synthesis effluent is decomposed for distilling off a gaseous mixture of a ammonia and carbon dioxide, regardless of whether the distilled gaseous mixture is recycled or not and of a manner of recycle.

In the present invention, a urea synthesis effluent which is discharged from a urea synthesis autoclave and which contains urea, unreacted carbamate and water is treated for decomposition of the unreacted ammonium carbamate into ammonia and carbon dioxide through a plurality of decomposition stages in which pressure is reduced by steps. The decomposition of the unreacted ammonium carbamate is effected in at least one high pressure decomposition stage at a gauge pressure of from 15 kg/cm$^2$ up to a pressure equal to a urea synthesis pressure and one low pressure decomposition stage at a gauge pressure of from 1 to 5 kg/cm$^2$, as well known in the art. The high pressure decomposition of the unreacted ammonium carbamate may be conducted by stripping with carbon dioxide or ammonia under a pressure substantially equal to the urea synthesis pressure, a high pressure rectification under a gauge pressure of 15 to 25 kg/cm$^2$, or by a two-stage decomposition composed of a decomposition stage of the unreacted ammonium carbamate under a gauge pressure of from 40 to 100 kg/cm$^2$ and a subsequent rectification stage under a gauge pressure of from 15 to 25 kg/cm$^2$.

The low pressure decomposition is generally effected by rectification in which a head temperature is preferred to be within a range of from 100° to 140° C. and a still temperature is preferred to be within a range of from 120° to 160° C. The low pressure rectification may be conducted by stripping with a small amount of carbon dioxide. The aqueous urea solution discharged from the low pressure rectification still contains a small amount of unreacted ammonium carbamate, so that it is preferable to subject the aqueous urea solution to flashing under an almost normal pressure for removal of most of the unreacted ammonium carbamate.

The aqueous urea solution substantially free of the unreacted ammonium carbamate is then fed to a concentration step wherein water is evaporated to form crystal urea or molten urea substantially free from water. The concentration is generally effected under vacuum or/and under a normal pressure. The water vapor generated in the concentration contains substantially all of ammonia and carbon dioxide which are contained in the urea aqueous solution, and a small amount of the urea aqueous solution mist. The water vapor is condensed in a condenser to form a dilute aqueous solution of ammonium carbamate and urea. This dilute aqueous solution is subjected to pressure rectification under a gauge pressure below 25 kg/cm$^2$, preferably to a low pressure rectification under a gauge pressure of from 1 to 5 kg/cm$^2$, for separation thereof into a gaseous mixture of ammonia and carbon dioxide and water free of ammonia and carbon dioxide. In the rectification, the head temperature is preferred to be within a range of from 110° to 180° C. and the still temperature within a range of from 120° to 230° C. By the rectification, part of water of the dilute aqueous solution is discharged from the urea synthesis system. For example, when the dilute aqueous solution contains water in an amount of from 98 to 99% (by weight), the water vapor content in the gaseous mixture of ammonia, carbon dioxide and water vapor which are distilled by rectification is preferred to be in the range of from 60 to 75% (by volume). In order to control a water content in the gaseous mixture in the rectification step, a condenser may be provided at the top of a rectifying column to allow a condensate of the distilled gaseous mixture to contact with a distilled gaseous mixture under suitable cooling conditions. With the rectification pressure above 25 kg/cm$^2$ (gauge), the rate of separation of ammonia from the aqueous solution is inferior.

The gaseous mixture of ammonia, carbon dioxide and water vapor from the rectification step is fed into a rectifying column for the urea synthesis effluent which operates under a gauge pressure below 25 kg/cm$^2$. The gaseous mixture is preferred to be fed into a tray of the rectifying column which is positioned 1 to 3 trays above a heating zone. In the case where a packed column is used as the rectifying column, the gaseous mixture may be fed into an inlet located at a position corresponding approximately to the above-mentioned tray. The gaseous mixture introduced into the rectifying column rises through the column and contacts with the urea synthesis effluent which flows downward from the top part thereof, whereby the water vapor is condensed and removed from the gaseous mixture. The ammonium carbamate in the urea synthesis effluent is decomposed into ammonia and carbon dioxide by heat of condensation which generates upon condensation of the water vapor. The ammonia and carbon dioxide contained in the gaseous mixture introduced into the rectifying column merely pass through the column. Accordingly, the mixed gas which is generated by the decomposition of unreacted ammonium carbamate, and ammonia and carbon dioxide of the introduced gaseous mixture is discharged from the top of the rectifying column without substantial increase in the water content when compared with that of the gaseous mixture generated by the decomposition of the unreacted ammonium carbamate, with the result that steam employed in the rectifying column can be saved in an amount corresponding to heat of condensation resulting from condensation of the water vapor contained in the gaseous mixture which is introduced into the rectifying column.

The present invention will be particularly illustrated with reference to the accompanying drawing, in which the sole FIGURE is a flow chart showing a preferred embodiment of the invention.

DESCRIPTION OF THE EMBODIMENTS

Referring to the figure, carbon dioxide, ammonia, and a recovered ammonium carbamate solution which will be described hereinlater are fed into a urea synthesis autoclave 4 from lines 1, 2 and 3, respectively, for reaction at a temperature of from 170° to 210° C. under a gauge pressure of from 150 to 300 kg/cm$^2$. The resultant urea synthesis effluent is passed through a line 5 to a pressure reducing valve 6 wherein its pressure is reduced to a lower level of from 15 to 25 kg/cm$^2$, and is introduced through a line 7 into the top part of a high pressure rectifying column 8. The high pressure rectifying column 8 is either provided with a plurality of trays or packed with a packing member such as a Raschig ring in an intermediate part thereof, and is provided with a heater 9 in the still thereof. The high pressure rectifying column is maintained at a temperature of from 120° to 160° C. at its head and at a temperature of from 140° to 180° C. at the still thereof. In column 8, a major part of the unreacted ammonium carbamate contained in the urea synthesis effluent is decomposed into ammonia, carbon dioxide and water vapor in the form of a gaseous mixture. The urea synthesis effluent discharged from the bottom of the high pressure rectifying column is fed through a line 10 to a pressure reducing valve 11 wherein the pressure is reduced to lower level of from 1 to 5 kg/cm$^2$ and is then passed into the top part of a low pressure rectifying column 13 through a line 12. In the low pressure rectifying column 13, there are provided trays or a packing member in the intermediate part thereof similarly to the high pressure rectifying column 8. Further, a heater 14 is provided in the still of the column 13. The low pressure rectifying column 13 is maintained at a temperature of from 100° to 140° C. at the head thereof and at a temperature of from 120° to 160° C. at the still thereof, so that remaining unreacted ammonium carbamate is mostly decomposed. The low pressure rectification may be effected in accordance with the method of the British Patent No. 1,295,742. The aqueous urea solution discharged from the bottom of the low pressure rectifying column 13 still contains unreacted ammonium carbamate in an amount, of as small as 2 to 3% (by weight) of the aqueous urea solution. The aqueous urea solution is passed through a line 15 to a pressure reducing valve 16 for reducing a pressure to a lower level of from 0 to 2 kg/cm$^2$ (gauge) and is flashed in the top part of a gas separator 18 through a line 17. The gas separator 18 may be provided with a packing member therein or may be provided with a heater at the bottom part thereof. The gas separator 18 is kept at a temperature of from 90° to 130° C. at the heat thereof, and most of the remaining unreacted substance is separated from the aqueous urea solution therein. The gas separation may be effected by stripping with air or may be carried out under vacuum.

The aqueous urea solution which is discharged from the gas separator 18 and which contains small amounts of ammonia and carbon dioxide is fed to a concentration zone 22 of a vacuum crystallizer through a line 19, a pressure reducing valve 20 and a line 21. The concentration zone 22 of the vacuum crystallizer is operated at an absolute pressure of from 50 to 100 mmHg, in which water is evaporated while precipitating urea as crystals. The amount of water to be evaporated is a total of an amount of water which is equivalent to water freshly produced in the synthesis autoclave 4 and of an amount of water which is introduced from the outside of urea synthesis system for use as an absorbent. As a heat source for the evaporation of said water, the heat of absorption of the gaseous mixture discharged from the high pressure rectification, as will be described hereinlater is used. The precipitated crystals are withdrawn in the form of slurry from the crystallization zone 22a of the vacuum crystallizer through a line 23, and is introduced into a centrifugal separator 24 for separation thereof from the mother liquor, followed by withdrawal thereof through a line 24a. The urea crystals or molten urea substantially free of water may be obtained by various methods as well as the vacuum crystallizing method. For example, the aqueous urea solution may be converted into crystal urea by a method wherein the aqueous urea solution from the line 21 is concentrated under a normal pressure and is fed to a crystallizer of a Swenson type to form crystalline urea, or the aqueous urea solution may be concentrated into molten urea substantially free of water under vacuum or normal pressure.

The water vapor from the concentration zone 22 of the vacuum crystallizer which contains small amounts of aqueous urea solution mist, ammonia and carbon dioxide is fed to a condenser 26 through a line 25 wherein the same is condensed by indirect heat exchange with cooling water which is fed from a line 27 and discharged from a line 28. Uncondensed water vapor is passed through a line 29 into an ejector 30 for vacuum generation together with uncondensed ammonia and carbon dioxide, and is then introduced into a barometric condenser 33 through a line 32 together with high pressure steam for driving the ejector which is fed through a line 31. In the barometric condenser 33, the uncondensed water vapor is completely condensed by contact with cooling water which is fed from a line 34.

The water vapor from the line 25 contains small amounts of inert gases, which are discharged from the barometric condenser 33. The condenser 26 may be one unit, or two or more units connected in series. When it is possible to condense substantially all of ammonia and carbon dioxide in the condenser 26, the barometric condenser 33 may be omitted. The water vapor may be passed into a suitable separator such as a cyclone separator equipped with a cooling jacket, prior to introduction thereof into the condenser 26, for separating the aqueous urea solution mist with condensation of part of water vapor. The resultant aqueous solution which contains urea, ammonia and carbon dioxide in low concentrations may be used as a wash water for crystal urea obtained by the centrifugal separation or as process water, such as an absorbent to be employed in an unreacted ammonia recovery step.

The condensate, which contains ammonia, carbon dioxide and urea is fed to a pump 37 through a line 35 together with the aqueous solution which is withdrawn from the barometric condenser 33 through a line 36 and contains small amounts of ammonia and carbon dioxide to raise the pressure to substantially the same level as that of the low pressure rectifying column 13. The condensate is then introduced into a heat exchanger 39 wherein it is heated by indirect heat exchange with hot water, as will be described in detail, and is fed to a tray located at a suitable position of an aqueous ammonium carbamate solution rectifying column 41. In the still of the rectifying column 41 a heater 42 is provided. The gaseous mixture of ammonia, carbon dioxide and water vapor is fed from the head of the column 41 and is introduced through a line 43 into a condenser 44 wherein the gaseous mixture is contacted with a condensate (which is an aqueous ammonium carbamate solution produced by condensation of the gaseous mixture fed from the line 43) which is maintained at a temperature of from 110° to 140° C. by cooling, thereby condensing part of the water vapor. A part of the condensed liquid is fed back from the condenser 44 through a line 45 into the top part of the aqueous ammonium carbamate solution rectifying column. The water vapor contained in the gaseous mixture from the rectifying column 41 is preferred to be present in as large an amount as possible since it is a heat source for the low pressure rectification. In the usual case, therefore, no reflux is effected. If reflux is conducted, the quantity of reflux should be kept to a minimum. From the still of the rectifying column 41 hot water having a temperature of from 120° to 230° C. and which contains a small amount of urea (while part of the urea contained in the aqueous solution fed from the line 40 is hydrolyzed) is discharged. This hot water is fed into the heat exchanger 39 through a line 46. In the heat exchanger 39, the hot water is cooled by indirect heat exchange with the aqueous solution to be fed into the aqueous ammonium carbamate solution rectifying column 41 and discharged from a line 47. When it is considered inconvenient from a viewpoint of environmental pollution to discharge, the hot water containing urea from the urea synthesis system, as it is the aqueous urea solution mist should be removed prior to the introduction of the water vapor from the concentration zone 22 of the vaccum crystallizer into the condenser 26 in a manner as described hereinbefore. It is to be noted that the gaseous mixture from line 48 may be fed into the high pressure rectifying column 8 without feeding it to the low pressure rectifying column 13.

The water vapor content in the gaseous mixture of ammonia and carbon dioxide fed from the condenser is, for example, in a range of from 60 to 75% (by volume) when the aqueous solution to be fed to the aqueous ammonium carbamate solution rectifying column 41 through the line 40 contains 98 to 99% (by weight) of water. The gaseous mixture is fed through a line 48 to a tray located just above or 1 to 3 trays above the heating zone of the low pressure rectifying column 13 and is contacted countercurrently with the urea synthesis effluent which runs downward from the top of the column, thereby condensing the water vapor in the mixed gas. The unreacted ammonium carbamate contained in the urea synthesis effluent is decomposed by heat of condensation generated upon the condensation of water vapor. The introduced gaseous mixture from which water vapor is partially removed by condensation is discharged from the head of the column along with a gaseous mixture of ammonia, carbon dioxide and water vapor which are produced by decomposition of the unreacted ammonium carbamate contained in the urea synthesis effluent.

The treatment of the gaseous mixtures of ammonia, carbon dioxide and water vapor discharged from the high pressure rectifying column 8, from the low pressure rectifying column 13 and from the gas separator 18, respectively, will be described hereunder. The gaseous mixture from the gas separator 18 is fed through a line 49 into a gas condenser 50 wherein it is contacted for condensation under cooling conditions with an absorbent such as water or an aqueous urea solution fed from a line 51 to form an aqueous ammonium carbamate solution. The thus formed aqueous ammonium carbamate solution is fed through a line 52 to a pump 53 to raise the pressure to 1 to 5 kg/cm² (gauge), followed by feeding through lines 54 and 55 into a low pressure absorption column 56. Simultaneously, a urea mother liquor which is separated by means of the centrifugal separator 24 and which is fed through a line 57 to a pump 58 wherein the pressure is raised to 1 to 5 kg/cm² (gauge) is fed into the low pressure absorption column 56 through lines 59 and 55. Further, part or all of the aqueous ammonium carbamate solution from the line 54 which is fed through a line 60 to combine with the condensate from the line 38 may be fed into the aqueous ammonium carbamate solution rectifying column 41 through the heat exchanger 39 and the line 40. By this, the absorbate obtained in the low pressure absorption column is prevented from being diluted.

Another gaseous mixture which is fed from the low pressure rectifying column 13 is passed into the low pressure absorption column 56 through a line 61 and is absorbed in the above-mentioned urea mother liquor and the aqueous ammonium carbamate solution under cooling. The resultant absorbate containing ammonium carbamate is fed through a line 62 to a pump 63 in which the pressure is raised to a gauge pressure of from 15 to 25 kg/cm² and is further fed to the top part of a high pressure absorption column 65 through a line 64. In the bottom part of the high pressure absorption column 65 a gaseous mixture from the high pressure rectifying column 8 through the line 66 is fed. In the high pressure absorption column 65, the gaseous mixture is contacted with and absorbed in the aqueous ammonium carbamate solution, which has flowed downward, under cooling by a cooler 67, and the remaining unabsorbed gaseous mixture is forcedly contacted with the aqueous ammonium carbamate solution flowing downward from the top part while rising through the column to allow all of carbon dioxide and part of ammonia to be absorbed therein. As a result, carbon dioxide-free ammonia gas is discharged from the head of the column. The ammonia gas is passed through a line 68 into an ammonia condenser 69 in which the same is cooled and liquefied. The resulting liquid ammonia is fed through a line 70 into the synthesis autoclave 4 together with make-up liquid ammonia from the line 2. Though cooling water may be passed through the cooler 67, the urea slurry from the crystallization zone 22a of the vacuum crystallizer may be passed therethrough into the concentration zone 22 of the vacuum crystallizer for use as a heat source by which water is evaporated from the urea slurry. From the bottom part of the high pressure absorption column 65 the recovered carbamate solution of high concentration is withdrawn, and the solution is fed through a line 71 into a pump 72 wherein the pressure is raised up to a gauge pressure of from 150 to 300 kg/cm² and is passed into the urea synthesis autoclave 4 through the line 3.

In the above embodiment, the gaseous mixture generated by decomposition of the unreacted ammonium carbamate may be recovered not only by absorption with an absorbent but also by a method wherein the gaseous mixture is adiabatically compressed by means of a compressor and fed to the urea synthesis autoclave in the form of a gas, or by cooling the gaseous mixture in liquid ammonia or oil to form a crystalline ammonium carbamate suspension.

According to the invention, most of the heat which is required for distilling ammonia and carbon dioxide as well as water vapor from a condensate of water vapor generated in concentrating an aqueous urea solution can be reused in rectification of unreacted ammonium carbamate contained in the urea synthesis effluent so as to reduce the quantity of steam to be consumed, and thereby hardly increasing steam consumption when considering the heat balance of the entirety of the urea production process. The absorption of a gaseous mixture from low pressure rectification of the condensate of water vapor generated in concentrating an aqueous urea solution is advantageous in that the quantity of heat to be removed by cooling is smaller than that required in a conventional method wherein a gaseous mixture distilled from the condensate is absorbed together with a gaseous mixture from low pressure rectification of the urea synthesis effluent, since excess water vapor does not enter into the absorption stage as in the conventional method.

The present invention will be particularly illustrated by way of the following example, in which parts are by weight.

EXAMPLE

The synthesis of urea from ammonia and carbon dioxide in a molar ratio of 4 was effected under a gauge pressure of 250 kg/cm$^2$ at a temperature of 200° C. to obtain a urea synthesis effluent, which was subjected to high pressure rectification at a gauge pressure of 17 kg/cm$^2$ and then to low pressure rectification at a gauge pressure of 2.5 kg/cm$^2$ at head and still temperatures of 105° C. and 130° C., respectively, to obtain an aqueous urea solution composed of 1,120 parts/hr of urea, 15 parts/hr of ammonia, 13 parts/hr of carbon dioxide, and 415 parts/hr of water. The aqueous urea solution was flashed into a gas separator to separate ammonia and carbon dioxide under a normal pressure at 110° C. As a result, the ammonia and carbon dioxide remaining in the aqueous urea solution were reduced to 5 parts/hr and 3 parts/hr, respectively. This solution was introduced into a concentration zone of a vacuum crystallizer operated under a absolute pressure of 80 mmHg at a temperature of 65° C. to crystallize out 1000 parts/hr of crystal urea in the crystallization zone of a vacuum crystallizer while evaporating 360 parts/hr of water vapor along with 4.6 parts of ammonia and 2.7 parts of carbon dioxide. The thus obtained crystal urea was separated from the mother liquor by means of a centrifugal separator. In the mother liquor, 0.4 parts/hr of ammonia and 0.3 parts of carbon dioxide were contained. The mother liquor was used for absorbent of ammonia and carbon dioxide fed from the low pressure rectifying column.

The gaseous mixture of water vapor, ammonia and carbon dioxide obtained by evaporation in the concentration zone of the vacuum crystallizer was passed into a surface condenser and cooled by water for condensation to produce a dilute aqueous ammonium carbamate solution of 37° C. In an ejector for vacuum generation inert gases were aspirated which were substantially free from ammonia and carbon dioxide, and saturated water vapor. The dilute aqueous ammonium carbamate solution from the surface condenser were composed of 4.5 parts/hr of ammonia, 2.7 parts/hr of carbon dioxide and 350 parts of water, and the pressure thereof was raised to 2.7 kg/cm$^2$ (gauge) by a pump. The aqueous solution was fed to an middle part of an aqueous ammonium carbamate solution rectifying column wherein the still and the head were maintained at 145° C. and 125° C., respectively. From the head, 4.6 parts/hr 2.7 parts/hr of carbon dioxide and 11 parts/hr of water were distilled in the form of a gaseous mixture.

This gaseous mixture was fed to a tray just above the heating zone of the low pressure rectifying column operated under a gauge pressure of 2.5 kg/cm$^2$. From the head of the low pressure rectifying column a gaseous mixture was distilled which was composed of 109.6 parts of ammonia, 52.7 parts/hr of carbon dioxide and 40.4 parts/hr of water vapor, and from the still an aqueous urea solution was discharged which was composed of 1,120 parts/hr of urea, 15 parts/hr of ammonia, 13 parts/hr of carbon dioxide and 425.6 parts/hr of water, i.e., an aqueous urea solution in which water increased by 10.6 parts/hr in comparison with a case where a gaseous mixture from the aqueous ammonium carbamate solution rectifying column was not introduced into the low pressure rectifying column. When the gaseous mixture from the aqueous ammonium carbamate solution rectifying column was not fed into the low pressure rectifying column, the distilled gas from the head thereof was composed of 105 parts/hr of ammonia, 50 parts/hr of carbon dioxide and 40 parts/hr of water vapor. The steam consumption in the low pressure rectifying column was 0.077 tons per ton of urea when the gaseous mixture from the aqueous ammonium carbamate solution was introduced into the rectifying column and 0.090 tons per ton of urea when the gaseous mixture was not introduced into the rectifying column.

What is claimed is:

1. In a process for treating water vapor generated in concentrating an aqueous urea solution wherein a urea synthesis effluent containing urea, unreacted ammonium carbamate and water from a urea synthesis zone is subjected to at least one high pressure unreacted ammonium carbamate decomposition stage and a low pressure unreacted ammonium carbamate decomposition stage provided with a low pressure rectifying zone, the pressure of said urea synthesis effluent is stepwise reduced in each stage to decompose substantially all of said unreacted ammonium carbamate into ammonia and carbon dioxide and to separate the formed mixture of ammonia, carbon dioxide and water vapor from the aqueous urea solution, the aqueous urea solution which still contains small amounts of ammonia and carbon dioxide is concentrated to obtain crystalline urea or molten urea substantially free of water, and water vapor which is generated in the concentration of said aqueous urea solution and which contains small amounts of ammonia and carbon dioxide is cooled for condensation to form a dilute aqueous ammonium carbamate solution, the improvement which comprises the steps of: (a) subjecting said dilute aqueous ammonium carbamate solution in an aqueous ammonium carbamate solution rectifying zone to rectification under a gauge pressure lower than 25 kg/cm$^2$ to distill off a gaseous mixture of water vapor, ammonia and carbon dioxide; (b) introducing said gaseous mixture into said low pressure rectifying zone of said low pressure unreacted ammonium carbamate decomposition stage operated under substantially the same pressure as the pressure in said aqueous ammonium carbamate solution rectifying zone in step (a) and at a head temperature of from 100° to 140° C. and a still temperature of from 120° C. to 160° C., thereby bringing said gaseous mixture into contact with said urea synthesis effluent in said low pressure rectifying zone, condensing and absorbing the water vapor contained in said gaseous mixture in said urea synthesis effluent to remove the water vapor from said gaseous mixture; and (c) recovering for recycling ultimately to the urea synthesis zone, the resultant gaseous mixture of ammonia and carbon dioxide together with a gaseous mixture of ammonia and carbon dioxide which is generated in said low pressure unreacted ammonium carbamate decomposition stage.

2. The improvement as claimed in claim 1, wherein the said water vapor generated in concentrating the said aqueous urea solution is condensed by indirect cooling with water.

3. The improvement as claimed in claim 2, wherein the aqueous urea solution mist contained in the said water vapor is separated prior to the condensation of the water vapor.

4. The improvement as claimed in claim 1, wherein the said water vapor generated in concentrating said aqueous urea solution is condensed by indirect cooling followed by mixing with water.

5. The improvement as claimed in claim 1, wherein the rectification of the said dilute aqueous ammonium carbamate solution is conducted at a gauge pressure of from 1 to 5 kg/cm$^2$.

6. The improvement as claimed in claim 1, wherein the rectification of the said dilute aqueous ammonium carbamate solution is conducted at a head temperature of from 110° to 180° C. and at a still temperature of from 120° to 230° C.

7. The improvement as claimed in claim 1, wherein a part of the gaseous mixture derived from the said aqueous ammonium carbamate solution rectifying zone is condensed and the resultant condensate is passed through the head of the aqueous ammonium carbamate solution rectifying zone to reduce the water content of the gaseous mixture.

8. The improvement as claimed in claim 1, wherein the dilute aqueous ammonium carbamate solution is heated by indirect heat exchange with hot water withdrawn from the aqueous ammonium carbamate solution rectifying zone.

9. The improvement as claimed in claim 1, wherein the gaseous mixture from the said aqueous ammonium carbamate solution rectifying zone is fed into said low pressure rectifying zone for decomposing unreacted ammonium carbamate at a gauge pressure of from 1 to 5 kg/cm$^2$.

* * * * *